(12) United States Patent
Popescu et al.

(10) Patent No.: US 6,744,846 B2
(45) Date of Patent: Jun. 1, 2004

(54) METHOD AND APPARATUS FOR AUTOMATIC EXPOSURE CONTROL IN CT SCANNING

(75) Inventors: Stefan Popescu, Erlangen (DE); Christoph Suess, Erlangen (DE); Heiko Wolf, Erlangen (DE); Dietmar Hentschel, Herzogenaurach (DE)

(73) Assignee: Siemens Aktiengesellschaft, Münich (DE)

( * ) Notice: Subject to any disclaimer, the term of this patent is extended or adjusted under 35 U.S.C. 154(b) by 32 days.

(21) Appl. No.: 10/255,356

(22) Filed: Sep. 26, 2002

(65) Prior Publication Data

US 2004/0062341 A1 Apr. 1, 2004

(51) Int. Cl.$^7$ ................................................. A61B 6/00
(52) U.S. Cl. ............................................. 378/16; 378/4
(58) Field of Search ....................................... 378/4–20

(56) References Cited

U.S. PATENT DOCUMENTS

| 5,400,387 A | | 3/1995 | Gard et al. ................. 378/207 |
| 5,485,494 A | * | 1/1996 | Williams et al. .............. 378/16 |
| 5,625,662 A | * | 4/1997 | Toth et al. .................... 378/16 |
| 5,696,807 A | | 12/1997 | Hsieh ........................... 378/109 |
| 5,822,393 A | | 10/1998 | Popescu ....................... 378/108 |
| 5,867,555 A | | 2/1999 | Popescu et al. ................ 378/16 |
| 6,094,468 A | * | 7/2000 | Wilting et al. .................. 378/8 |
| 6,507,639 B1 | | 1/2003 | Popescu ....................... 378/108 |

OTHER PUBLICATIONS

"Noise Due to Photon Counting Statistics in Computed X–ray Tomography," Chesler et al., J. of Computer Assisted Tomography, vol. 1, No. (1977) pp. 64–74.

* cited by examiner

*Primary Examiner*—Craig E. Church
*Assistant Examiner*—Jurie Yun
(74) *Attorney, Agent, or Firm*—Schiff Hardin LLP

(57) ABSTRACT

In a computed tomography apparatus and a method for automatic exposure control in computed tomography scanning, an exposure controller, during a first half of a revolution of an X-ray focus around a subject, calculates an actual attenuation profile of a slice of the subject from electrical signals generated by the radiation detector in the first half of the revolution, and calculates an extrapolated attenuation profile of the slice for a second half of the revolution from the actual attenuation profile, and adjusts an operating parameter of the X-ray source, such as the tube current, to modify the radiation dose emitted by the X-ray source during the second half of the revolution dependent on the extrapolated attenuation profile.

20 Claims, 2 Drawing Sheets

METHOD AND APPARATUS FOR AUTOMATIC EXPOSURE CONTROL IN CT SCANNING

BACKGROUND OF THE INVENTION

1. Field of the Invention

The present invention is directed to a method for automatically controlling the exposure during a CT (computed tomography) scan, as well as to an apparatus for automatically controlling the exposure in CT scanning.

2. Description of the Prior Art

Computed tomography systems of the last generation have enhanced the ability to perform large volume scans over a significant region of the body of an examination subject. This capability has improved the efficiency of CT installations, by shortening the examination time and thereby increasing the patient throughput. During relatively long examinations, such as spiral (helical) examinations, which cover a large volume of the body of the subject, the radiation absorption by the patient changes significantly along the spiral path. Without undertaking additional measures, however, the CT system would employ X-rays of a constant intensity along the entirety of the scanned volume. When the shoulder-chest region of the patient is being scanned, for example, the radiation absorption by the patient in the shoulder slices is very high, thereby necessitating a high X-ray intensity in order to obtain low noise images. When scanning the lungs, however, at a different slice location along the longitudinal length of the body, this X-ray intensity may be excessive, because the lungs have a very low density and thus exhibit weak X-ray absorption.

It is highly desirable to have good quality images with a reasonable X-ray exposure, and therefore a need has been recognized for automatic exposure control in these types of relatively long duration scans. Such automatic exposure control is for the purpose of adjusting the X-ray intensity in each slice, according to the patient absorption which prevails in the body region for which the region is being obtained.

In conventional radiographic imaging, automatic exposure control is a standard feature that avoids the use of an insufficient X-ray dose, or a higher then necessary X-ray dose. Many users of CT systems are requesting automatic exposure control in such systems in order to reduce the total dose to which a patient is exposed.

Several methods are known for implementing automatic exposure control during long-duration CT scans, i.e., scans consisting of many rotations around the body of the patient, wherein many slice image are generated. Three basic approaches have conventionally been employed for this purpose.

One of these approaches is based on information acquired prior to a main scan, i.e., information acquired in a so-called scout scan. This technique is exemplified by U.S. Pat. No. 5,400,387. In this known technique, two orthogonal scout (topographic) scans are conducted over the entirety of the body segment that is to be subsequently diagnostically scanned. Based on the attenuation information obtained by these scout scans, and dependent on target pixel noise, the system calculates the appropriate tube current for the X-ray tube for each slice in the main scan. This method has the disadvantage of requiring an extra radiation dose to be applied to the patient during the scout scans. This known technique also necessitates a longer overall examination time, thus reducing the throughput of the CT installation. Moreover, the information provided by the scout scans may not be sufficient to allow the appropriate tube current to be calculated, if the scout scans, for example, failed to identify the maximum or minimum patient absorption for each slice. Usually the scout scans are performed so as to obtain a lateral view or an anterior-posterior view, but it is known that for some body regions, such as the abdomen region, the maximum and minimum patient absorption are best identified at other (different) viewing angles. Moreover, in general terms the use of only two orthogonal views is insufficient to completely define the patient absorption profile around a complete slice, as is required for a fully accurate calculation of the tube current. Moreover, this known technique also will produce inaccurate results, if the patient's body moves between the scout scans and the main scan.

A further known technique is to undertake automatic exposure control using a negative feedback loop, which includes the X-ray tube and the voltage and current generator which feeds the X-ray tube, as well as one or more detectors. This technique is described in U.S. Pat. No. 5,696,807. In this known technique, a feedback controller measures an average signal from an X-ray detector (conventionally called photon saturation), and adjusts the tube current in order to minimize any deviation between a predetermined, desired signal level and the actual signal level. The predetermined signal level is calculated in advance, in order to achieve a specified target noise. A disadvantage of this known technique is that it has limited practical application, since it is well-known that the X-ray beam emitted by a conventional X-ray tube does not become modified sufficiently quickly, due to the thermal inertia of the heating system of the X-ray tube, to allow tracking of rapid changes in the tube current. In other words, after a change in the tube current is made, there is a time delay until X-rays are actually emitted at a level corresponding to the changed current. It is also known that the patient absorption profile exhibits rapid changes as the tube rotates around the patient. A negative feedback system, which would modulate the tube current following the patient absorption profile necessitates a higher modulation speed of the X-ray tube, and thus cannot be implemented with conventional CT X-ray tubes. The remedy of slowing down the response time of the feedback controller, in order to accommodate the slow modulation capability of the X-ray tube, usually will cause problems in the overall system response. In such a situation, the radiation profile being currently employed will not match the actual patient absorption profile, thereby resulting either in an increased image noise or an inefficient X-ray dose.

A third known technique is to undertake exposure control based on statistical data and user entries, as described in U.S. Pat. No. 6,094,468. In this method, the appropriate tube current is calculated based on statistical data regarding the expected patient absorption within various anatomical body regions, and/or based on geometric measurements of the patient's size and dimensions, taking corrective inputs made by an operator into account. Therefore, this technique cannot be classified as a truly automatic exposure control, but instead is a pre-programmed modulation of the dose profile, and therefore this method may not necessarily achieve the best results. This technique is dependent on the prediction accuracy of the patient absorption, which may vary significantly from patient-to-patient. This system also is dependent on the skill and knowledge of the operator in deciding on and entering the appropriate corrective inputs.

SUMMARY OF THE INVENTION

It is an object of the present invention to provide a method and an apparatus for undertaking automatic exposure control in a CT scan, wherein the aforementioned disadvantages of known systems and techniques are avoided or at least minimized.

This object is achieved in accordance with the principles of the present invention in a computed tomography apparatus, and in a method for operating a computed tomography apparatus, wherein at least the focus of an X-ray source is rotated through at least one revolution around an examination subject for conducting a CT scan of the subject, and wherein a control arrangement is connected to a radiation detector, on which an X-ray beam emitted by the X-ray source is incident after being attenuated by an examination subject, and to the X-ray source, and wherein the control arrangement, during a first half of the revolution, calculates an attenuation profile of a portion of the subject from electrical signals generated by the radiation detector in the first half of the revolution, and calculates an extrapolated attenuation profile for a second half of the revolution from the actual attenuation profile, and adjusts at least one operating parameter of the X-ray source during the second half of the revolution dependent on the extrapolated attenuation profile. The adjustment of at least one parameter of the X-ray source in the second half of the revolution can be undertaken with the goal of achieving a target pixel noise in each slice image. This target noise may be different for each body region or for each examination protocol. The respective target noise values for different body regions and/or different examination protocols can be stored in a memory in default tables, or can be selectively specified by an operator of the CT system through an interface. If a relatively long spiral or sequential CT scan is to be undertaken, different target noise values can be set for different slice locations along the longitudinal length of the scan, dependent on the different attenuation profiles of the body regions which are successively scanned. Thus, for each body region, i.e. for each slice image, an appropriate X-ray dose is employed in order to generate a good quality image, while not exposing the examination subject to an unnecessarily high radiation dose when this is not needed for good image quality.

The operating parameter of the X-ray source which is adjusted can be the X-ray tube current. In order to achieve the target pixel noise for the slice image, the exposure controller automatically adjusts the X-ray tube current once per each half-revolution in the scan. The tube current required for the target pixel noise is calculated based on the X-ray absorption profile during the previous half-revolution, and is extrapolated for the next half-revolution. The control of the tube current is undertaken by taking into account the delay associated with the X-ray tube response, and the tube current is set by means of a prediction so that the desired X-ray intensity is reached at the correct time, taking the delay into account. This prediction is required to compensate for the slow response of conventional X-ray tubes. A suitable method and apparatus for modulating a parameter of an X-ray tube, taking the modulation speed of the X-ray tube into account, are disclosed in U.S. Pat. No. 6,507,639, the teachings of which are incorporated herein by reference.

As supported by analysis of patient data, the attenuation profile of a patient does not change significantly between successive half-revolutions, and therefore the aforementioned extrapolation of the attenuation profile can be undertaken with acceptable accuracy. A software algorithm evaluates the attenuation profile of the previous half-revolution, and calculates the operating parameter, such as the X-ray tube current, appropriate for the exposure in the next half-revolution. During the first half-revolution in the scan, the software algorithm "learns" the actual attenuation profile and sets the tube current to a nominal value based thereon. The algorithm also samples and integrates the attenuation profile of the half-revolution currently being scanned, and processes this information to calculate and predict the tube current necessary to achieve the target noise for the next half-revolution.

Moreover, the patient attenuation profile does not change significantly between successive projections (i.e., successive revolutions), and therefore alternatively the exposure controller can evaluate only every $N^{th}$ projection in order to calculate the extrapolated attenuation profile, where N>1.

Moreover, within a single projection it may be sufficient to detect only the maximum average attenuation that dominates the total sum over the projection, instead of making a calculation for each ray position within the projection.

The automatic exposure method and apparatus described herein can be combined with known techniques for modulating the dose as a function of the exposure angle within a single revolution, as described in U.S. Pat. No. 5,867,555.

DESCRIPTION OF THE PREFERRED EMBODIMENTS

Figure 1:
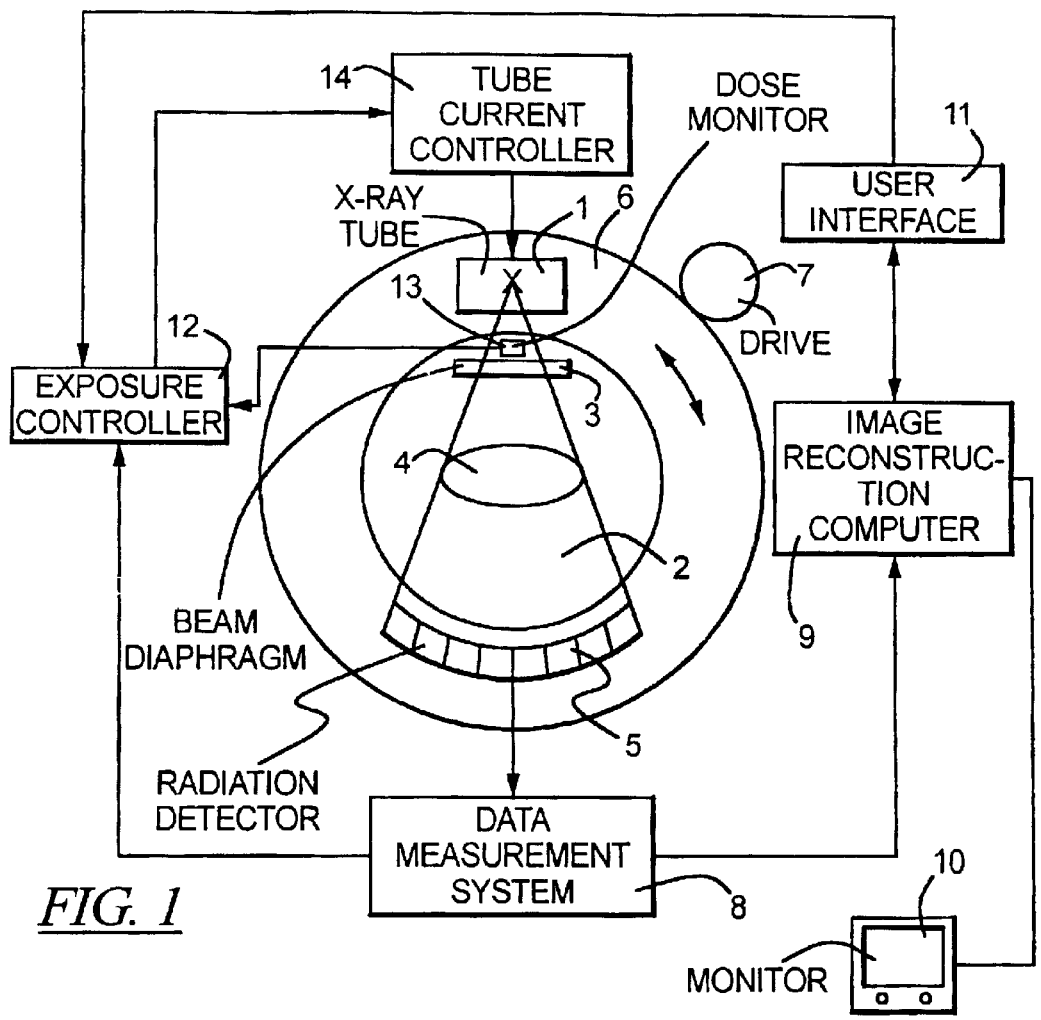
FIG. 1 is a schematic block diagram of a CT apparatus including automatic exposure control, constructed and operating in accordance with the principles of the present invention.

The computed tomography system shown in FIG. 1 has an X-ray tube 1 which emits an X-ray beam 2 from a focus. The X-ray beam 2 is gated by a beam diaphragm 3, and proceeds through an examination subject 4, so as to be incident on a radiation detector 5. The X-rays incident on the radiation detector 5, therefore, are attenuated by the examination subject 4, and the radiation detector 5 generates electrical signals corresponding to the attenuated X-ray incident thereon.

In the embodiment shown in FIG. 1, the X-ray tube 1 and the radiation detector 5 are mounted on a rotatable gantry 6, which is rotated by a drive 7. The X-ray beam 2 is therefore caused to rotate around the examination subject 4, so that a series of projections, respectively obtained at different projection angles, are made. Each projection has a dataset of the aforementioned electrical signals associated therewith. These datasets are supplied from the radiation detector 5, for each projection, to a data measurement system 8 for collection and editing, and the datasets are supplied from the data measurement system 8 to an image reconstruction computer 9, which constructs a CT image of the examination subject 4 from the projection data in a known manner. This image is displayed on a monitor 10 connected to the computer 9.

The system also includes a user interface 11 which is connected to the image reconstruction computer 9. The image reconstruction computer 9 in this embodiment therefore also serves as the system control computer and will therefore include connections in a known manner (which are not shown) to various component such as the drive 7 a voltage supply for the X-ray tube 1, embodied in a tube current controller 14, and the beam diaphragm 3. Alternatively, a separate control computer can be used for this purpose.

In accordance with the invention the system shown in FIG. 1 also includes an exposure controller 12 and a dose monitor 13. The exposure controller 12 receives a signal from the dose monitor 13, which is disposed in the X-ray beam 2, indicating the intensity of the X-rays before being attenuated by the examination subject 4. The exposure controller 12 also receives signals from the data measurement system 8, representing the attenuated X-rays, so that the exposure controller 12 can calculate an attenuation profile of the patient 4 from the signals from the dose monitor 13 and the data measurement system 8. As explained in more detail below, the exposure controller 12 calculates an actual attenuation profile during a first half-revolution of the X-ray tube 1 around the examination subject, and, based on that actual attenuation profile, calculates an extrapolated attenuation profile for the second half of that revolution. Based on this extrapolated attenuation profile, the exposure controller 12 adjusts at least one operating parameter of the X-ray tube 1. In the exemplary embodiment shown in FIG. 1, this parameter is the tube current, and therefore the exposure controller 12 is shown as supplying a control signal to the tube current controller 14. As noted above, however, the tube current controller 14 is embodied in a voltage supply for the X-ray tube 1, which supplies the X-ray tube 1 with all necessary operating voltages and currents. The tube current is the primary operating parameter related to X-ray intensity, and therefore the X-ray dose, however, any operating parameter of the X-ray tube 1 which contributes to the radiation dose can be controlled in accordance with the invention.

Also in the embodiment shown in FIG. 1, the exposure controller 12 is shown as being directly connected to the user interface 11 so that an operator, via the user interface 11, can enter control settings into the exposure controller 12 to selectively determine the manner and frequency by which the attenuation profiles are calculated. It is not necessary however, that a direct connection from the user interface 11 to the exposure controller 12 be used for this purpose, such settings can be entered via the user interface 11 and supplied to the exposure controller 12 by the system control computer, whether embodied in the image reconstruction computer 9 or as a separate computer.

Figure 2:
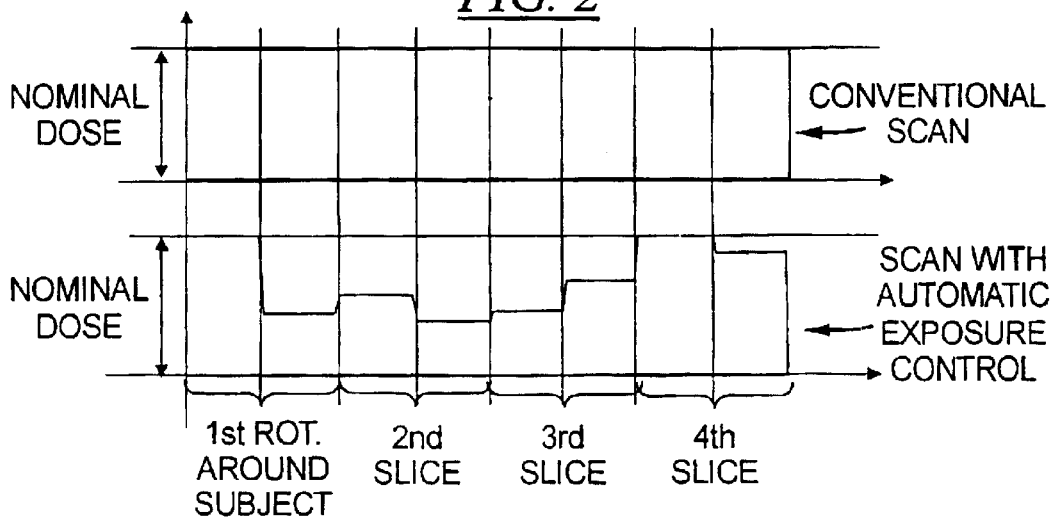
FIG. 2 illustrates the dose produced using the automatic exposure control of the invention, and compares it with a nominal dose employed in a conventional CT scan.

An example of how the X-ray dose is adjusted in accordance with the invention is shown in FIG. 2, in the lower portion thereof designated scan with automatic exposure control. As can be seen, in a first half rotation or revolution of the X-ray tube 1 around the examination subject 4, a nominal X-ray dose is employed. Based on the actual attenuation profile calculated in this first half rotation, an extrapolated attenuation profile is calculated, and is used by the exposure controller 12 to control the tube current controller 14, so as to adjust the tube current during the second half of the first rotation.

During this second halt of the first rotation, the attenuation profile is again calculated and is then used by the exposure controller 12 to control the tube current controller 14 to appropriately adjust the tube current during the first half of the next rotation of the X-ray tube 1 around the examination subject 4, which is used to produce a second slice image. This procedure is repeated for all successive slices, with only the third and fourth additional slices being shown in FIG. 2.

The dose achieved in accordance with the invention is contrasted in FIG. 2 with the nominal dose which is constantly employed in a conventional scan, as shown in the upper portion of FIG. 2.

Figure 3:
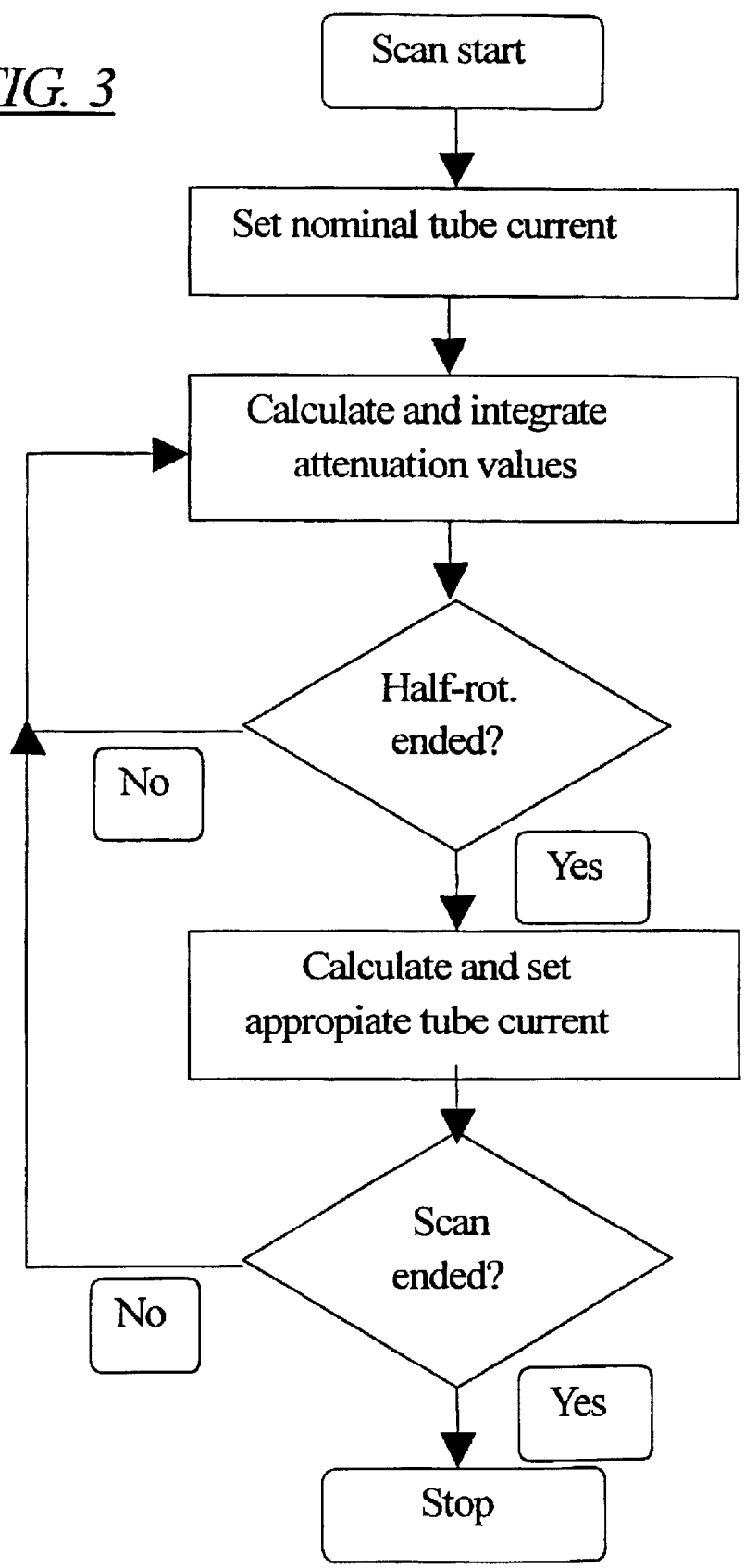
FIG. 3 is a flowchart of a basic embodiment of the automatic exposure control in accordance with the inventive method.

This procedure is set forth in the flowchart of FIG. 3, which illustrates a basic embodiment for the software algorithm employed in the exposure controller 12. In a first step, a start of a scan is recognized, and the aforementioned nominal tube current is then set. Attenuation values using this nominal tube current are then calculated and integrated during a first half rotation. These values are calculated in a loop which continually interrogates whether the current half-revolution has ended. If the answer to the inquiry is negative, the loop is repeated. If the answer to this inquiry is affirmative, then the exposure controller 12 calculates and sets an appropriate tube current, and supplies this calculated tube current as a control signal to the tube current controller 14. This calculation can be undertaken by the exposure controller 12 in a manner which takes into account the modulation speed of the X-ray tube 1, i.e., the delay which the X-ray tube 1 exhibits in producing a modification of the emitted X-ray beam 2 upon a change in an operating parameter, such as the tube current.

The exposure controller 12 then determines when the total scan has ended, based on the values entered via the user interface 11 characterizing the type of scan being conducted. If the scan has not ended, the aforementioned procedure for calculating the tube current is repeated. If the scan has ended, the procedure is at an end.

For determining whether each half-revolution has ended and for determining whether the scan has ended, any suitable known technique can be used by the exposure controller 12, depending on the information which is supplied thereto via the user interface 11. Assuming that the X-ray tube 1 is rotated at a constant speed around the examination subject 4, the beginning and end of each half rotation, and the end of the scan, can be indicated simply as a time count. Alternatively, the exposure controller 12 can have a direct connection to the drive 7 so that a tachometer or rotational encoder signal can be supplied from the drive 7 to the exposure controller 12, or the exposure controller 12 can receive direct signals from the system control computer, either as a separate computer or embodied in the image reconstruction computer 9.

As noted above, the automatic exposure control can be undertaken so as achieve a target pixel noise in each slice image. As disclosed in "Noise Due to Photon Counting Statistics in Computed X-ray Tomography," Chesler et al., J. of Comp. Assist. Tomog., Vol. 1, No. 1 (1977) pp. 64–74, the variance (σ) of quantum noise that results within an image element of a CT scan can be derived from the patient adsorption and the applied dose. The theoretical equation that predicts the total pixel noise as a function of the total quantum noise of each projection used to reconstruct the slice image is:

$$\sigma_{total}^2 = \sigma_1^2 + \sigma_2^2 + \ldots + \sigma_N^2 \qquad (1)$$

Wherein N is the total number of projections used for the reconstruction, and $\sigma_1$ is the quantum noise in each projection (i=1 ... N). The total quantum noise $_{projection}$ for a given projection depends on the signal noise in each detector (measurement channel) of the radiation detector 5, according to the following relation:

$$\sigma_{protection}^2 = \sigma_1^2 + \sigma_2^2 + \ldots + \sigma_M^2 \qquad (2)$$

wherein M is the total number of channels measured in the projection.

The signal noise in each detector channel depends on the tube current, the exposure time (X-ray dose) and the slice width as follows:

$$\sigma^2 = K \cdot \frac{A}{Dose \cdot Slice} = K \cdot \frac{A}{I_{TUBE} \cdot T \cdot Slice} \quad (3)$$

wherein K is a constant for a scan dependent on the high voltage of the X-ray tube 1, the system geometry, and the reconstruction kernel employed in the reconstruction algorithm in the image reconstruction computer 9, A is the attenuation for the current exposure ray proceeding from focus of the X-ray tube 1 to the radiation detector 5, Dose is the MaS product for the current measurement and Slice is the width of the radiation detector 5 along the system axis around which the X-ray tube 1, or its focus, rotates (slice thickness).

Based on the above equations, the tube current required to achieve a target pixel noise $\sigma_{target}$ in the final image is related to the exposure and the patient absorption as follows:

$$I_{TUBE} = K \cdot \frac{\sum_t A_t}{\sigma_{target}^2 \cdot Slice \cdot T} \quad (4)$$

Wherein T is the exposure time (referred to as integration time in CT terminology), and the other terms are as identified above.

Therefore, in order to estimate the necessary tube current for achieving the target noise, the software algorithm in the exposure controller 12 must calculate and integrate (accumulate) the patient attenuation for each exposure ray in each projection.

Thus, based on the signals received from the data measurement system 8 and the dose monitor 13, the exposure controller 12 calculates the patient absorption for each detector element and projection (examination ray) as $$A_t = \frac{U_{mon}}{U_t} \quad (5)$$

Wherein $U_i$ is the signal for channel i and $U_{mon}$ is the reference monitor signal from the dose monitor 13. During a half-rotation, the exposure controller 12 accumulates all of these attenuation values. When a half-rotation is completed, the exposure controller 12 calculates the required tube current for the current slice, using the target pixel noise, obtained by an entry made via the user interface 11, and generates a control signal for the tube current controller 14 to modulate the tube current as needed. During this accumulation process, the running sum may override the previous accumulated value, in which case the tube current must be increased for the next half-rotation. As noted above, the exposure controller 12 can take the modulation speed (delay) of the X-ray tube 1 into account in the timing of the generation of the appropriate control signal.

Although the exemplary embodiment described above has been in the context of a CT apparatus of the type wherein both the X-ray tube and the radiation detector are rotatable around the examination subject, it will be apparent that the inventive method and control apparatus are suitable for use with a CT apparatus of any generation, including system wherein only the X-ray tube rotates around the subject, or wherein only the focus of the X-ray tube rotates around the subject.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography apparatus comprising:
   an X-ray source which emits an X-ray beam from a focus, said X-ray source having at least one operating parameter which determines a radiation dose associated with said X-ray beam;
   a radiation detector on which said X-ray beam is incident, said X-ray source and said radiation detector being adapted to receive a subject therebetween so that said X-ray beam is incident on said radiation detector after being attenuated by said subject, said radiation detector generating electrical signals dependent on X-rays incident thereon;
   at least said focus being rotatable through at least one revolution around said subject to conduct a CT scan wherein said electrical signals form projection data for a slice of said subject;
   a computer supplied with said projection data for reconstructing an image of said slice therefrom; and
   a control arrangement connected to said radiation detector and to said X-ray source for, during a first half of said revolution, calculating an actual attenuation profile of said slice from said electrical signals generated in said first half of said revolution and for calculating an extrapolated attenuation profile of said slice for a second half of said revolution from said actual attenuation profile, and for adjusting said at least one operating parameter to modify said radiation dose during said second half of said revolution dependent on said extrapolated attenuation profile.

2. A computed tomography apparatus as claimed in claim 1 wherein said image is comprised of a plurality of pixels having pixel noise associated therewith, and wherein said control arrangement adjusts said at least one operating parameter dependent on said extrapolated attenuation profile to set said radiation dose to achieve a target pixel noise.

3. A computed tomography apparatus as claimed in claim 1 further comprising a user interface connected to said control arrangement allowing a user to enter a selected value for said target pixel noise.

4. A computed tomography apparatus as claimed in claim 2 wherein at least said focus of said X-ray source is rotatable through a plurality of revolutions around said subject to conduct a spiral CT scan, composed of a plurality of slices, and wherein each of said slices has a respective target pixel noise associated therewith, and wherein said control arrangement adjusts said at least one operating parameter dependent on said extrapolated attenuation profile during scanning of the respective slices to achieve the respective target pixel noise for the respective slices.

5. A computed tomography apparatus as claimed in claim 4 wherein said control arrangement includes a memory wherein values for the respective target pixel noise for the slices in said helical CT scan are stored.

6. A computed tomography apparatus as claimed in claim 1 wherein said X-ray source has a tube current associated therewith, and wherein said control arrangement adjusts said tube current as said at least one operating parameter.

7. A computed tomography apparatus as claimed in claim 1 wherein said control arrangement includes a dose monitor disposed in said X-ray beam on which said X-ray beam is incident before being attenuated by said subject, said dose monitor generating a monitor output signal dependent on the X-rays in said X-ray beam incident thereon, and wherein said control arrangement further comprises an exposure controller connected to said dose monitor and to said radiation detector, said exposure controller calculating said actual attenuation profile from said electrical signals generated by said radiation detector and from said monitor output signal.

8. A computed tomography apparatus as claimed in claim 1 wherein said X-ray source has a modulation speed associated therewith at which said X-ray source modifies said radiation dose dependent on a change in said at least one operating parameter, and wherein said control arrangement adjusts said at least one operating parameter in advance dependent on said modulation speed.

9. A computed tomography apparatus comprising:
an X-ray source which emits an X-ray beam from a focus, said X-ray source having a tube current which determines a radiation dose associated with said X-ray beam;
a radiation detector on which said X-ray beam is incident, said X-ray source and said radiation detector being adapted to receive a subject therebetween so that said X-ray beam is incident on said radiation detector after being attenuated by said subject, said radiation detector generating electrical signals dependent on X-rays incident thereon;
at least said focus being rotatable through at least one revolution around said subject to conduct a CT scan wherein said electrical signals form projection data for a slice of said subject;
a computer supplied with said projection data for reconstructing an image of said slice therefrom, said image being composed of a plurality of pixels having pixel noise associated therewith;
a dose monitor disposed in said X-ray beam on which said X-ray beam is incident before being attenuated by said subject, said dose monitor generating a monitor output signal dependent on X-rays in said X-ray beam incident thereon;
a tube current controller connected to said X-ray tube for adjusting said tube current; and
an exposure controller connected to said radiation detector, said dose monitor and said tube current controller, said exposure controller, during a first half of said revolution, calculating an actual attenuation profile of said slice from said monitor output signal and said electrical signals generated during said first half of said revolution, and calculating an extrapolated attenuation profile for a second half of said revolution from said actual attenuation profile to achieve a target pixel noise in said second half of said revolution, said exposure controller supplying a control signal, at least at a beginning of said second half of said revolution, to said tube current controller for adjusting said tube current, and thereby modifying said radiation dose, during said second half of said revolution.

10. A computed tomography apparatus as claimed in claim 9 wherein at least said focus is rotatable through a plurality of revolutions around said subject to conduct a spiral CT scan to obtain respective sets of projection data for a plurality of slices of said subject, each of said slices having a target pixel noise, and wherein said exposure controller calculates said extrapolated attenuation profile for a second half of each of said revolutions dependent on the respective target pixel noise for the slice currently being scanned.

11. A method for operating a computed tomography apparatus comprising the steps of:
emitting an X-ray beam from a focus of an X-ray source, said X-ray source having at least one operating parameter which determines a radiation dose associated with said X-ray beam;
detecting said X-ray beam with a radiation detector on which said X-ray beam is incident;
disposing a subject between said X-ray source and said radiation detector so that said X-ray beam is incident on said radiation detector after being attenuated by said subject, said radiation detector generating electrical signals dependent on X-rays incident thereon;
rotating at least said focus through at least one revolution around said subject to conduct a CT scan wherein said electrical signals form projection data for a slice of said subject;
supplying a computer supplied with said projection data and reconstructing an image of said slice therefrom; and
in a control arrangement connected to said radiation detector and to said X-ray source, during a first half of said revolution, calculating an actual attenuation profile of said slice from said electrical signals generated in said first half of said revolution and calculating an extrapolated attenuation profile of said slice for a second half of said revolution from said actual attenuation profile; and
adjusting said at least one operating parameter to modify said radiation dose during said second half of said revolution dependent on said extrapolated attenuation profile.

12. A method as claimed in claim 11 wherein said image is comprised of a plurality of pixels having pixel noise associated therewith, and comprising adjusting said at least one operating parameter dependent on said extrapolated attenuation profile to set said radiation dose to achieve a target pixel noise.

13. A method as claimed in claim 12 further comprising entering a selected value for said target pixel noise via a user interface connected to said control arrangement.

14. A method as claimed in claim 11 comprising rotating at least said focus of said X-ray source through a plurality of revolutions around said subject to conduct a spiral CT scan, composed of a plurality of slices, and wherein each of said slices has a respective target pixel noise associated therewith, and control adjusting said at least one operating parameter dependent on said extrapolated attenuation profile during scanning of the respective slices to achieve the respective target pixel noise for each of the respective slices.

15. A method as claimed in claim 14 wherein comprising storing values for the respective target pixel noise for the slices in said helical CT scan in a memory in said control arrangement.

16. A method as claimed in claim 11 wherein said X-ray source has a tube current associated therewith, and comprising adjusting said tube current as said at least one operating parameter.

17. A method as claimed in claim 11 comprising disposing a dose monitor in said X-ray beam on which said X-ray beam is incident before being attenuated by said subject, said dose monitor generating a monitor output signal dependent on the X-rays in said X-ray beam incident thereon, and wherein said control arrangement further comprises an exposure controller connected to said dose monitor and to said radiation detector, and in said exposure controller calculating said actual attenuation profile from said electrical signals generated by said radiation detector and from said monitor output signal.

18. A method as claimed in claim 11 wherein said X-ray source has a modulation speed associated therewith at which said X-ray source modifies said radiation dose dependent on a change in said at least one operating parameter, and comprising adjusting said at least one operating parameter in advance dependent on said modulation speed.

19. A method for operating a computed tomography apparatus comprising the steps of:

emitting an X-ray beam from a focus of an X-ray source, said X-ray source having a tube current which determines a radiation dose associated with said X-ray beam;

detecting said X-ray beam with a radiation detector on which said X-ray beam is incident;

disposing a subject between said X-ray source and said radiation detector so that said X-ray beam is incident on said radiation detector after being attenuated by said subject, said radiation detector generating electrical signals dependent on X-rays incident thereon;

rotating at least said focus through at least one revolution around said subject to conduct a CT scan wherein said electrical signals form projection data for a slice of said subject:

supplying a computer supplied with said projection data and reconstructing an image of said slice therefrom, said image being composed of a plurality of pixels having pixel noise associated therewith;

disposing a dose monitor in said X-ray beam on which said X-ray beam is incident before being attenuated by said subject, said dose monitor generating a monitor output signal dependent on X-rays in said X-ray beam incident thereon;

adjusting said tube current with a tube current controller connected to said X-ray tube; and in an exposure controller connected to said radiation detector, said dose monitor and said tube current controller, during a first half of said revolution, calculating an actual attenuation profile of said slice from said monitor output signal and said electrical signals generated during said first half of said revolution, and calculating an extrapolated attenuation profile for a second half of said revolution from said actual attenuation profile to achieve a target pixel noise in said second half of said revolution; and supplying a control signal, at least at a beginning of said second half of said revolution, from said exposure controller to said tube current controller for adjusting said tube current, and thereby modifying said radiation dose, during said second half of said revolution.

20. A method as claimed in claim 19 comprising rotating at least said focus through a plurality of revolutions around said subject to conduct a spiral CT scan to obtain respective sets of projection data for a plurality of slices of said subject, each of said slices having a target pixel noise, and calculating in said exposure controller, said extrapolated attenuation profile for a second half of each of said revolutions dependent on the respective target pixel noise for the slice currently being scanned.

* * * * *